United States Patent [19]

Semeraro et al.

[11] Patent Number: 5,011,848
[45] Date of Patent: * Apr. 30, 1991

[54] 1.4-DIHYDRO PYRIDINES

[75] Inventors: Claudio Semeraro, Bresso; Dino Micheli, Carpi; Daniele Pieraccioli; Giovanni Gaviraghi, both of Verona, all of Italy; Allan D. Borthwick, London, England

[73] Assignee: Glaxo, S.p.A., Verona, Italy

[*] Notice: The portion of the term of this patent subsequent to Jan. 31, 2006 has been disclaimed.

[21] Appl. No.: 300,022

[22] Filed: Jan. 23, 1989

Related U.S. Application Data

[62] Division of Ser. No. 767,593, Aug. 20, 1985, Pat. No. 4,801,599.

[30] Foreign Application Priority Data

Aug. 22, 1984 [IT] Italy .............................. 22383 A/84
Jul. 5, 1985 [IT] Italy .............................. 21460 A/85

[51] Int. Cl.$^5$ ......................................... A61K 31/455
[52] U.S. Cl. ..................................... 514/356; 546/321
[58] Field of Search ......................... 546/321; 514/356

[56] References Cited

U.S. PATENT DOCUMENTS 4,801,599 1/1989 Semeraro et al. .................. 546/321

OTHER PUBLICATIONS

Rahwan et al.-Annual Reports in Medicinal Chem.-16, 1981, pp. 257-266.

*Primary Examiner*—Jane T. Fan

*Attorney, Agent, or Firm*—Morgan & Finnegan

[57] ABSTRACT

Compounds are described of the formula

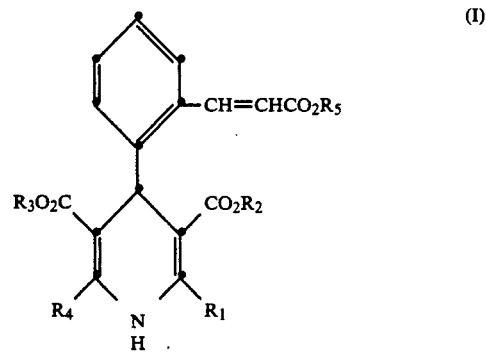

wherein
$R_1$ and $R_4$ independently represent a $C_{1-4}$ alkyl group;
$R_2$ and $R_3$ independently represent a $C_{1-6}$ straight or branched alkyl chain which may be interrupted by an oxygen atom;
$R_5$ represents a straight or branched chain $C_{1-13}$ alkyl group or a $C_{5-8}$ cycloalkyl group which may be substituted by a $C_{1-3}$ alkyl substitutent;

The compounds represented by formula (I) reduce intracellular calcium ion concentration by limiting transmembranal calcium ion influx and thus may be useful for the treatment of cardiovascular disorders such as hypertension.

27 Claims, No Drawings

1,4-DIHYDRO PYRIDINES

This is a divisional of co-pending application Ser. No. 767,593 filed Aug. 20, 1985 now U.S. Pat. No. 4,801,599 issued Jan. 31, 1989.

This invention relates to novel heterocyclic derivatives which have an effect on the transmembranal influx of calcium ions into the cells of cardiac and smooth muscle, to processes for the preparation thereof, to pharmaceutical compositions containing them and to their use in therapeutics.

The role of intracellular calcium ions in the control of the contractile system of cardiac and smooth muscle is well known. Furthermore it has been established that compounds which limit the intracellular calcium ion concentration by preventing or reducing the transmembranal calcium ion influx in cells of the contractile system of cardiac and smooth muscle are useful in the treatment of cardiovascular disorders.

We have now found a new group of compounds which reduce intracellular calcium ion concentration by limiting transmembranal calcium ion influx and thus may be useful for the treatment of cardiovascular disorders such as hypertension, angina pectoris, myocardial ischaemia, congestive heat failure, cerebral vascular and peripheral disorders.

The invention thus provides for compounds of the general formula (I).

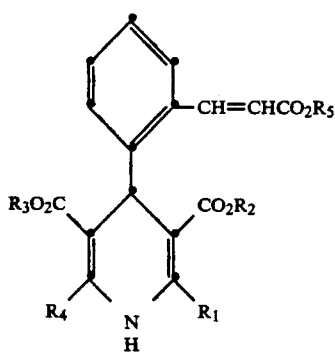

(I)

wherein $R_1$ and $R_4$ independently represent a $C_{1-4}$ alkyl group;

$R_2$ and $R_3$ independently represent a $C_{1-6}$ straight or branched alkyl chain which may be interrupted by an oxygen atom;

$R_5$ represents a straight or branched chain $C_{1-13}$ alkyl group or a $C_{5-8}$ cycloalkyl group which may be substituted by a $C_{1-3}$ alkyl substitutent;

The compounds represented by formula (I) can exist in more than one isomeric and/or enantiomeric form and the invention includes all such isomers, enantiomers and mixtures thereof. Thus the group —CH=CH-CO$_2$R$_5$ is compounds of formula (I) can exist in the cis (Z) or the trans (E) configuration and the invention includes both isomers and mixtures thereof.

Examples of suitable groups for $R_2$ and $R_3$ independently include $C_{1-4}$ straight or branched alkyl such as methyl, ethyl, isopropyl, isobutyl, t-butyl or $C_{1-4}$ alkyl (such as methyl, ethyl or n-propyl) substituted by a $C_{1-3}$ alkoxy e.g. methoxy or propoxy group.

When the group $R_5$ represents a $C_{1-13}$ alkyl group this may for example include methyl, ethyl, propyl, isopropyl, butyl, isobutyl, sec butyl, tert butyl, pentyl, isopentyl, neopentyl, hexyl, 2,6-dimethyl-4-heptyl, octyl and tridecyl groups. When $R_5$ represents a cycloalkyl group, conveniently this represents cyclopentyl, cyclohexyl and cycloheptyl, which cycloalkyl groups may be substituted by a $C_{1-3}$ alkyl group e.g. a methyl group. Preferred compounds of formula (I) are those in which the group CH=CHCO$_2$R$_5$ exists in the (E) configuration.

Preferred meanings for the groups $R_1$ and $R_4$ independently include ethyl or more particularly methyl.

$R_2$ and $R_3$ preferably independently represent $C_{1-4}$ alkyl e.g. methyl, ethyl, isopropyl or isobutyl or ethyl substituted by $C_{1-3}$ alkoxy e.g. methoxy or propoxy.

$R_5$ preferably represents $C_{3-9}$ straight or branched alkyl such as isopropyl, tert butyl, 2,6-dimethyl-4- heptyl or octyl, or $C_{5-7}$ cycloalkyl e.g. cyclopentyl or cyclohexyl which may be substituted by a methyl group.

A particularly preferred class or compounds of the invention are those of formula I wherein $R_1$ and $R_4$ represent methyl, $R_2$ and $R_3$ independently represent methyl, ethyl, isopropyl, isobutyl, propoxyethyl or methoxyethyl and $R_5$ represents $C_{3-9}$ alkyl, more particularly isopropyl, tert butyl, 2,6- dimethyl-4-heptyl or octyl, or a cyclohexyl group which may be substituted by a methyl group.

Within this particularly preferred class of compounds those where $R_5$ represents a tertiary butyl group are especially preferred.

A particularly preferred compound according to the invention is 4-(2-(3-(1,1-dimethylethoxy)-3-oxo-1-propenyl) phenyl)-1,4-dihydro-2,6-dimethyl-3,5-pyridinedicarboxylic acid, diethyl ester and more especially the E isomer thereof.

Other preferred compounds according to the invention are 4-(2-(3-(1,1-dimethylethoxy)-3,5-oxo-1-propenyl)-phenyl)-1,4-dihydro-2,6-dimethyl-3,5 -pyridinedicarboxylic acid, 3-methyl ester, 5-(2-methylpropyl) ester;

4-(2-(3-(1,1-dimethylethoxy)-3-oxo-1propenyl)phenyl)-1,4-dihydro -2,6-dimethyl-3,5-pyridinedicarboxylic acid, dimethyl ester;

4-(2-(3-(1,1-dimethylethoxy)-3-oxo-1-propenyl)phenyl-1,4-dihydro -2,6-dimethyl-3,5-pyridinedicarboxylic acid, 3-methyl ester 5-ethyl ester;

and more particularly the E isomers thereof.

The compounds of the invention limit intracellular ion concentrations by preventing or reducing the transmembranal calcium ion influx in cells. Thus for example the compounds limit or inhibit the effect of calcium ion on the tone of depolarised vascular smooth muscle.

The antihypertensive activity of the compounds of the invention was demonstrated by intravenous and/or oral administration of the compound to male spontaneously hypertensive rats. In these tests compounds of the invention and more especially the specific compounds named above have been found to have a particularly advantageous profile of activity including a relatively long duration of action.

The compounds of the invention are thus of interest in the treatment of hypertension. They are also potentially useful for the treatment of other cardiovascular disorders including angina pectoris, myocardial ischaemia, congestive hat failure, cerebral vascular and peripheral disorders. They may be formulated in a conventional manner with one or more pharmaceutical carriers.

Thus a further aspect of the invention includes pharmaceutical compositions of the compounds of formula (I) formulated for oral, sub lingual, transdermal, parenteral or rectal administration.

For oral administration the pharmaceutical composition may take the form of for example tables, which may be film or sugar coated, capsules, powders, granules, solutions including syrups, or suspensions prepared by conventional means with acceptable excipients. For sub lingual administration the composition may take the form of tablets or lozenges formulated in conventional manner.

For parenteral administration the compounds of formula (I) may be given as a bolus injection or by continuous infusion. The compositions may take such forms as suspension, solutions or emulsions in oily or aqueous vehicles and may contain formulatory agents such as suspending, stabilising and/or dispersing agents. For administration by injection these may take the form of a unit dose presentation or as a multidose presentation preferably with an added preservative.

Alternatively for parenteral administration the active ingredient may be in powder form for reconstitution with a suitable vehicle.

The compounds of formula (I) may be formulated as ointments and creams for transdermal administration and as suppositories or retention enemas for rectal administration.

A proposed daily dosage of active compound of the invention for the treatment of man is in the range of 0.005 mg to 50 mg for example 0.01 mg to 20 mg, which may conveniently be administered in one or more doses. The precise dose employed will depend on the age and condition of the patient as well as the route of administration.

For oral use the compounds of the invention are conveniently administered to the human patient at a dose in the range 0.01 to 50 mg, more preferably 0.1 to 20 mg per day. For parenteral use the compounds of the invention are conveniently administered at a dose in the range of 0.005 to 1 mg, more preferably 0.01–0.5 mg per day.

For oral use the compound is preferably administered twice or more particularly once a day.

Methods for preparing the compounds of formula (I) are described below and for the intermediates described below $R_1$, $R_2$, $R_3$, $R_4$, and $R_5$, have the meanings defined above for compounds of formula (I) or are such groupings in a protected form.

Thus compounds of formula (I) and more particularly the E isomers thereof, may be prepared by reaction the $\alpha,\beta$-unsaturated ketone (II) with the aminoester (III). The reaction is conveniently carried out in a solvent such as an alkanol, e.g. ethanol or isopropanol and preferably with heating e.g. 40°–150° C.

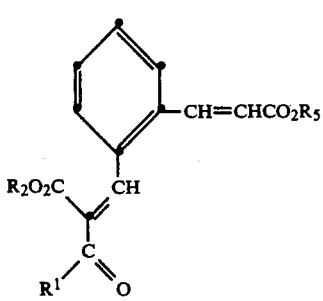

(II)

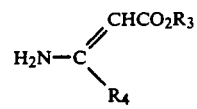

(III)

The $\alpha$, $\beta$-unsaturated ketone (II) may be prepared by reacting the aldehyde (IV) with the ketoester (V), in a solvent such as an alkanol e.g. ethanol or isopropanol, preferably with heating e.g. 40°–150° C. Conveniently this reaction is carried out in the presence of a catalyst such as piperidine acetate.

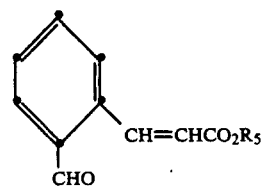

(IV)

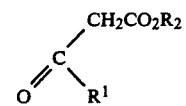

(V)

In a modification of this process for preparing compounds of formula (I), the aldehyde (IV) may be reacted with a mixture of the aminoester (III) and the ketoester (V) under the conditions previously described for the reaction of the $\alpha,\beta$-unsaturated ketone (II) with the aminoester (III).

Compounds of formula (I) and in particular the E isomers thereof in which $R_1$ and $R_4$ are the same and $R_2$ and $R_3$ are the same may be prepared by reacting the aldehyde (IV) with the aminoester (III) in the presence of a suitable acid catalyst. Examples of suitable acid catalysts include organic acids such as oxalic acid, alkanoic acids e.g. acetic acid or haloalkanoic acids such as trichloroacetic acid or trifluoroacetic acid or pyridinium salts thereof, or a sulphonic acid such as an alkanesulphonic acid e.g. methanesulphonic acid or an arylsulphonic acid e.g. benzenesulphonic acid or p-toluenesulphonic acid or a tetrahaloboric acid such as tetrafluoroboric acid. The reaction is preferably carried out in the presence of a solvent and at a temperature within the range of $-70°$ to $30°$ preferably $-30°$ to $10°$ C. Suitable solvents for the reaction include aprotic solvents such as hydrocarbons, e.g. hexane or cyclohexane, acetonitrile or ethers such as tertiary butyl methyl ether, dioxan or tetrahydrofuran, or protic solvents such as an alkanol e.g. methanol, ethanol, propanol, isopropanol or butanol.

Compounds of formula (I) and more particularly the E isomers thereof in which $R_1$ and $R_4$ are the same and $R_2$ and $R_3$ are the same may also be prepared by reacting the aldehyde (IV) with the ketoester (V) and ammonium acetate. This reaction is conveniently carried out in a solvent such as pyridine with heating at 50°–120° C., conveniently at reflux.

In a further process of the invention compounds of formula (I) may be prepared by esterifying the corresponding acid of formula (I) in which $R_5$ is hydrogen. Thus is one embodiment of this process compounds of formula (I) may be prepared by treating a compound of formula (I) in which $R_5$ is hydrogen with an alkylating agent $R_5X$ where $R_5$ is as defined in formula (I), and X is a leaving group such as chloride, bromide, iodide or mesylate. The reaction is preferably carried out in the presence of a base such as an alkali or alkaline earth metal carbonate e.g. potassium carbonate in a polar aprotic solvent such as dimethylformamide or dimethylsulphoxide optionally with heating. Thus for example the reaction may be carried out a temperature within the range 10°-100°.

In a further embodiment of this process compounds of the invention may be prepared from the corresponding carboxylic acid of formula (I) in which $R_5$ is hydrogen, via an activated derivative thereof such as a mixed anhydride, by reaction with an appropriate alcohol $R_5OH$, where $R_5$ is as defined in formula (I), or the corresponding alkoxide thereof.

The compounds of formula (I) wherein $R_5$ represents hydrogen may be prepared by hydrolysis of a compound of formula (I) wherein $R_5$ represents a tertiary butyl group. The hydrolysis may be carried out using hydrogen bromide in acetic acid, in the presence of a solvent such as dichloromethane. Preferably the reaction is carried out at low temperatures e.g. −78°-35° C.

In yet another process of the invention the E isomers of compounds of formula (I) may be prepared by treating a compound of formula (VI)

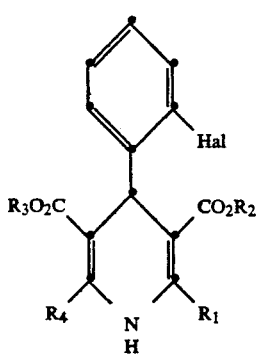

(VI)

(where Hal represents a bromine or iodine atom) with an acrylic ester $CH_2=CHCO_2R_5$ (VII), in the presence of a catalytic amount of a palladium salt such as palladium acetate, in the presence of a suitable organic base such as a trialkylamine e.g. triethylamine or tri-n-butylamine. The reaction is also preferably carried out in the presence of a triarylphosphine such as tri-o-tolyphosphine, or more preferably, triphenylphospine.

The reaction is conveniently carried out in a suitable solvent such as xylene or t-butyl acetate, or more conveniently in dimethylformamide or in a mixture of solvents e.g. xylene/dimethylformamide, preferably with heating. The reaction mixture is preferably heated within the temperature range of 80° C. to 150° C., more preferably at 100° C. to 110° C.

The carboxylic acids represented by the compounds of formula (I) wherein $R_5$ represents hydrogen are new compounds and useful chemical intermediates for preparing the compounds of formula (I) and represent a further feature of the invention.

Compounds of formula (IV) may be prepared by reacting the bis aldehyde (VIII) with the triphenylphosphorane (IX) in solvent such as methylene chloride or toluene.

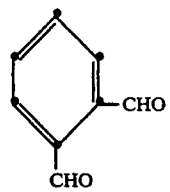

(VIII)

$Ph_3P=CHCO_2R_5$ (IX)

Compounds of formula (IV) may also be prepared by reacting a 2-halobenzaldehyde (X)

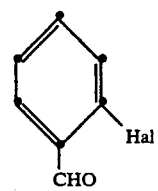

(X)

(where Hal represents a bromine or iodine atom) with an acrylic ester (VII). The reaction takes place under the conditions previously described for the reaction between the compound of formula (VI) and the acrylic ester (VII).

The compounds of formula (VI) may be prepared by reacting the 2-halobenzaldehyde (X) with the aminoester (III) and/or the ketoester (V) according to the conditions described above for the reaction between the compound of formula (IV) and the aminoester (III) and/or the ketoester (V).

The compounds of formulae (III), (V), (VII), (VIII), (IX) and (X) are either known compounds or may be made by analogous processes to those used for known compounds.

Compounds of formula (I) in which the group $-CH=CHCO_2R_5$ is in the cis (Z) configuration may be prepared by irradiating a solution of the corresponding trans (E) isomer. Thus when a solution of the E isomer in dichloromethane under a atmosphere of nitrogen is exposed to daylight a mixture of the E and Z isomers are obtained and these may be separated by standard techniques such as fractional crystallisation and/or chromatography.

Compounds of formula (I) may also be prepared from the reaction of the compound (XI) with the phosphorane (IX) in a suitable solvent such as dichloromethane, tetrahydrofuran or toluene. Preferably the reaction is carried out with heating for example 40°-120° C., conveniently at reflux.

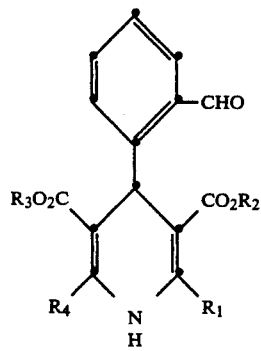

(XI)

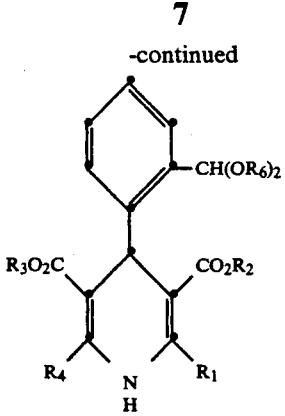

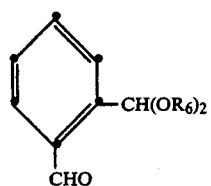

The intermediate (XI) may be prepared by aqueous acid hydrolysis of the corresponding acetal (XII; in which $R_6$ represents an alkyl group)

the compound of formula (XII) may be prepared from the aldehyde (XIII) by reaction with a compound of formula (III) and/or (V) under the conditions described above for preparing compounds of formula (I) from the intermediate (IV). The intermediate (XIII) may be prepared from the bromobenzene derivative (XIV) by reaction with butyl lithium in solvent followed by addition of dimethylformamide.

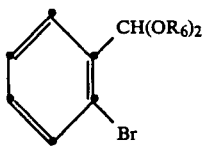

The following examples illustrate the invention. Throughout the example reference to t.l.c. means thin layer chromatography on Merck silica gel 60F-254. All temperature refer to °C.

INTERMEDIATE 1

1a. (E)-3-(2-Formylphenyl)-2-propenoic acid, 1,1-dimethyl ethyl ester

A solution of triphenylphosphoranylidene acetic acid 1,1-dimethylethyl ester (54.7 g) in dry dichloromethane (100 ml) was added to a solution of ortho phthaldehyde (19.3 g) in dry dichloromethane at 0° C. in 15 minutes. The solvent was evaporated and the oil taken up with diethyl ether. The solid triphenylphosphine oxide was filtered, washed with ether and the filtrate evaporated to dryness to give a yellow oil (36 g), which was eluted on a silica gel column (petrol ether/diethylether, 7:3), to give the title compound as a colourless oil (21.4 g). T.l.c. (Petrol Ether/diethyl ether, 1:1) Rf=0.45.

1b.

In a similar manner (E)-3-(2-formylphenyl)-2-propenoic acid, ethyl ester (12 g) was prepared from o-phthaldehyde (13.4 g) and triphenylphosphoranylidene acetic acid ethyl ester (34.8 g).

T.l.c. (Petrol ether/diethyl ether, 1:1) Rf=0.40.

INTERMEDIATE 2

2-(Diethoxymethyl)bromobenzene

A mixture of 2-bromobenzaldehyde (33.2 g), triethyl orthoformate (29 g) and powdered ammonium chloride (0.379 g) in ethanol (30 ml) was stirred for eight hours at room temperature. The resulting suspension was filtered and the filtrate evaporated. The resulting yellow oil was distilled at reduced pressure to give the title compound (31 g). b.p. 63° C. 0.3 mm Hg. T.l.c. (Petrol/diethyl ether, 6:1) Rf=0.6.

INTERMEDIATE 3

2-(Diethoxymethyl)benzaldehyde

To a solution of tetrahydrofuran (250 ml) and ether (250 ml) was added a 1.2M solution of butyl lithium in hexane (160 ml). The mixture was stirred and cooled to −70° C. and then Intermediate 2 (50 g) was added dropwise. After the addition the mixture was stirred at −70° for 30 minutes and then a solution of dimethylformamide (165 ml) in tetrahydrofuran (75 ml was added slowly dropwise keeping the temperature at −65°. A saturated aqueous solution of ammonium chloride (150 ml) was added, the organic phase separated and the aqueous phase extracted with ether (2×70 ml). The combined organic phase was dried (MgSO₄) and evaporated. The resulting brown oil was distilled at reduced pressure to give the title compound (30 g) as a white waxy solid. b.p. 87° C. 0.9 mm Hg. T.l.c. (Petrol/diethyl ether, 7:3) Rf=0.6.

INTERMEDIATE 4

4-(2-Formylphenyl)-1,4-dihydro-2,6-dimethyl-3,5-pyridinecarboxylic acid, diethyl ester To a stirred solution of ethyl-3-aminocrotonate (9.3 g) in glacial acetic acid (5 ml) at 0° was added dropwise Intermediate 3 (5 g). After two hours the reaction was poured into ethyl acetate (100 ml) and shaken with 10% hydrochloric acid. The organic phase was separated, dried (MgSO₄) and evaporated. The residual brown oil was purified by column chromatography (silica gel, dichloromethane/ethyl acetate 7:3) and crystallized from diethyl ether to give the title compound (0.200 g) as a yellow solid. m.p. 172°–173°. T.l.c. (Petrol/ethyl acetate, 7:3) Rf=0.4.

INTERMEDIATE 5

4-(2(2-Carboxyethenyl)phenyl)-1,4-dihydro-2,6-dimethyl-3,5-pyridinedicarboxylic acid, diethyl ester To a solution of the compound of Example 1 (10 g) in dichloromethane (70 ml), at −78° C. was added slowly, a solution of HBr/CH₃COOH 33% in dichloromethane (70 ml). The mixture was then warmed to −35° C. and after 10 minutes poured into ice/water. The pH was adjusted at 6 and the mixture extracted with ethyl acetate, washed with water and dried over Na₂SO₄. Evaporation of the solvent gave a solid which was recrystallized from petrol ether/ethyl acetate (1:1) to give the title compound as a white solid (6.5 g). T.l.c. (CH₂Cl₂/CH₃CO₂C₂H₅/CH₃COOH, 8:2:1) Rf=0.4. m.p. 175°–178°

INTERMEDIATE 6

6a. 2,6-Dimethyl-4heptylmethanesulphonate

A solution of methanesulphonyl chloride in diethyl ether was added dropwise to a solution of 2,6-dimethyl-4-heptanol and triethylamine in ether at 0° C. The mixture was then stirred for 2 hrs at room temperature, then poured into water and extracted with ether. The organic phase was washed with dilute hydrochloric acid, then water and dried over $Na_2SO_4$. Evaporation of the solvent gave the title compound (2.6 g) as a colourless oil. T.l.c. (Ethyl acetate/cyclohexane, 4:6). Rf.=0.55. Similarly prepared was:

6b. 2-Methylcyclohexylmethanesulphonate

T.l.c.(methylene chloride/Ethyl acetate, 7:3) Rf.=0.75. From methanesulphonyl chloride and 2-methylcyclohexane

INTERMEDIATE 7

4-(2-Bromophenyl)-1,4-dihydro-2,6-dimethyl-3,5-pyridinecarboxylic acid, diethyl ester (a) A solution of 2-bromobenzaldehyde (83.7 g) in absolute ethanol (1350 ml) was cooled to −10° under stirring. To the solution trifluoroacetic acid (108 g) was added quickly followed by a solution of ethyl 3-aminocrotonate (146 g) in ethanol (750 ml) added dropwise during 1 hour. Stirring was continued for a further 1 hour at −10° and the mixture was then added dropwise to a 0.3% solution of hydrochloric acid (7000 ml) under vigorous stirring. The solid was collected by filtration, washed with water and petroleum ether and dried in vacuo at 60° to give the title compound (156 g). m.p. 142°–143°. T.l.c. (ethyl acetate/petroleum ether, 8:2) Rf=0.5

(b) A solution of 2-bromobenzaldehyde (10.8 g), ethyl 3-aminocrotonate (9.36 g) and ethyl acetoacetate (9.12 g) in absolute ethanol (50 ml) was heated at reflux for 15 hours. The mixture was then cooled, diluted with absolute ethanol (250 ml) and added dropwise to a 0.2% solution of hydrochloric acid (2000 ml) under vigorous stirring. The solid was collected by filtration, washed with petroleum ether (150 ml) and dried in vacuo to give the title compound (19.3 g) m.p. 142°–143°.

INTERMEDIATE 8

4-(2-Iodophenyl)-1,4-dihydro-2,6-dimethyl-3,5-pyridinecarboxylic acid, diethyl ester Following the procedure in Intermediate 7(a) 2-iodobenzaldehyde (46.4 g) and ethyl 3-aminocrotonate (73 g) gave the title compound (54.8 g) m.p. 178°. T.l.c. (dichloromethane/ethyl acetate, 9:1) Rf=0.5.

INTERMEDIATE 9

2-(2-(3-(1,1-Dimethylethoxy)-3-oxo-1-propenyl)-phenyl)methylene-3-oxo-butanoic acid, methyl ester A solution of piperidine (0.11 g) and acetic acid (0.078 g) in iospropanol (1 ml) was added to a solution of 3-(2-formylphenyl)propenoic acid 1,1-dimethylethyl ester (5.2 g) and methyl acetoacetate (2.55 g) in isopropanol (15 ml). The mixture was stirred at 60° C. for 1h, then the solvent was evaporated and the residue taken up with ether (100 ml). The solution was washed with 1N HCl, water, with saturated bicarbonate solution, then water again and dried over $Na_2SO_4$. Evaporation of the solvent gave an oil which was purified by column chromatography (gradient Petrol/Ether, 7:3 −1:1) to give the title compound as a pale oil (4.2 g; mixture E/Z isomers).

Example 1

(E)-4-(2-(3-(1,1-Dimethylethoxy)-3-oxo-1-propenyl)-phenyl)-1,4-dihydro-2,6-dimethyl-3,5-pyridinedicarboxylic acid, diethyl ester Ethyl 3-aminocrotonate (24 g) was added to a solution of Intermediate 1a (21.4 g) in acetic acid, at room temperature. The red solution was stirred at room temperature for 5 hrs, then poured into water and extracted with ethyl acetate. The organic phase was washed with 5% aqueous sodium bicarbonate solution, then with water and dried over $Na_2SO_4$. Evaporation of the solvent gave a dark oil, which was eluted on a silica gel column ($CH_2Cl_2$/Ethyl acetate, 9:1). The title compound was obtained as a white solid (3.6 g) and recrystallized from ethyl acetate, m.p. 173°–175° C. T.l.c. (methylene chloride/Ethyl acetate, 9:1) Rf.=0.4

EXAMPLE 2

4-(2-(3-(1,1-Dimethylethoxy)-3-oxo-1-propenyl)-phenyl)-1,4-dihydro-2,6-dimethyl-3,5-pyridinedicarboxylic acid, diethyl ester To a solution of Intermediate 4 (0.1 g) in dichloromethane (0.5 ml) was added triphenylphosphoranylidene acetic acid 1,1-dimethylethyl ester (0.1 g) in dichloromethane (0.5 ml) at room temperature. After 12 hours reflux in dichloromethane, tetrahydrofuran was added and refluxing continued for 12 hours. Then toluene was added and the mixture refluxed for a further 5 hours. The mixture was evaporated and the residue purified by column chromatography and crystallized from petrol to give the title compound (120 mg) as a mixture of E and Z isomers.

EXAMPLE 3

(E)-4-(2-(3-Ethoxy-3-oxo-1-propenyl)phenyl)-1,4-dihydro-2,6dimethyl-3,5-pyridinedicarboxylic acid, diethyl ester Ethyl 3-aminocrotonate (13 g) was added to a solution of Intermediate 1b (10.2 g) in acetic acid (150 ml), at room temperature. The red solution was stirred at room temperature for 3 hrs., then poured into water and extracted with ethyl acetate. The organic phase was washed with 5% aqueous sodium bicarbonate solution, then with water and dried over $Na_2SO_4$. Evaporation of the solvent gave a dark oil (20 g), which as eluted on a silica gel column ($CH_2Cl_2$/Ethyl acetate, 7:3). The title compound was obtained as a white sole (4.5 g) and recrystallized from petrol ether/diethyl ether (9:1); m.p. 130°–131° C.; T.l.c. (methylene chloride/Ethyl acetate, 8:2) Rf=0.50

EXAMPLE 4

4a.

(E)-4-(2-(3-(1,1-dimethylethoxy-3-oxo-1-propenyl)-phenyl)-1,4-dihydro-2,6-dimethyl-3,5-pyridinedicarboxylic acid 3-methyl ester, 5-ethyl ester Intermediate 1a (0.5 g), ethyl 3-aminocrotonate (0.27 g) and methyl acetoacetate (0.24 g) in ethanol were refluxed for 14 hrs. The solvent was then evaporated and the crude oil was eluted on a silica gel column (diethyl ether/petrol ether 7:3) to yield the title compound as a pale yellow solid (0.25 g), m.p. 165°–167° C. (petrol ether). T.l.c. (Diethyl ether/petrol ether, 9:1) Rf=0.3

Similarly prepared were:

4b.
(E)-4-(2-(3-(1,1-dimethylethoxy)-3-oxo-1-propenyl)phenyl) -1,4-dihydro-2,6-dimethyl-3,5pyridinedicarboxylic acid 3-methyl ester, 5-(2-methylpropyl) ester m.p. 147°–149° (petrol ether) T.l.c. (Petrol ether/ethyl acetate 6:4) Rf=0.35 From Intermediate 1a, methyl 3-aminocrotonate and 2-methylpropyl acetoacetate

4c.
(E)-4-(2-(3-(1,1-dimethylethoxy)-3-oxo-1-propenyl)phenyl) -1,4-dihydro-2,6-dimethyl-3,5-pyridinedicarboxylic acid, 3-(1-methylethyl) ester, 5-(2-methoxyethyl) ester m.p.=156°–157° C. (petrol ether)
T.l.c. (ethyl acetate/cyclohexane, 1:1) Rf=0.35 From Intermediate 1a, 1-methylethyl 3-aminocrotonate and 2-methoxyethyl acetoacetate

4d.
(E)-4-(2-(3-(1,1-dimethylethoxy)-3-oxo-1-propenyl)phenyl -1,4-dihydro-2,6-dimethyl-3,5-pyridinedicarboxylic acid, dimethyl ester m.p.=158°–162° (petrol ether/diethyl ether, 100:1). T.l.c. (petrol/ethyl acetate, 6:4) Rf=0.25 From Intermediate 1a, methyl 3-aminocrotonate and methyl acetoacetate

4e.
(E)-4-(2-(3-(1,1-dimethylethoxy)-3-oxo-1-propenyl)phenyl) -1,4-dihydro-2,6-dimethyl-3,5-pyridinedicarboxylic acid, bis-2-n-propoxyethyl ester m.p.=115–116 (petrol/ether)
T.l.c. (ethyl acetate/cyclohexane 1:1) Rf=0.40 From Intermediate 1a, n-propoxyethyl 3-aminocrotonate and n-propoxyethyl acetoacetate

4f.
(E)-4-(2-(3-Ethoxy-3-oxo-1-propenyl)phenyl)-1,4-dihydro -2,6-dimethyl-3,5-pyridinedicarboxylic acid ethyl (1,1-dimethyl)ethyl ester From Intermediate 1b, 3-oxobutanoic acid ethyl ester and 3-aminobutenoic acid 1,1-dimethylethyl ester.

EXAMPLE 5

5a.
(E)-4-(2-(3-Octyloxy-3-oxo-1-propenyl)phenyl)-1,4-dihydro -2,6-dimethyl-3,5-pyridinedicarboxylic acid, diethylester A suspension of the Intermediate 5 (0.5 g), octyl bromide (0.38 g) and potassium carbonate (10 g) was stirred at room temperature for 20 hrs. The mixture was poured into water and extracted with ethyl acetate, washed thoroughly with water and dried over Na$_2$SO$_4$.

Evaporation of the solvent gave an oil which was triturated with petrol ether and recrystallized from petrol ether to give the title compound as a white solid (0.3 g), m.p. 110–°112°. T.l.c. (methylene chloride/ethyl acetate, 9:1) Rf=0.5

Similarly were prepared:

5b. (E)
-4-(2-(3-Methoxy-3-oxo-1-propenyl)phenyl)-1,4-dihydro-2,6-dimethyl -3,5-pyridinedicarboxylic acid, diethyl ester m.p. 138°–140° (petrol ether). T.l.c. (methylene chloride/Ethyl acetate 8:2) Rf=0.40 From Intermediate 5 and methyl bromide.

5c.
(E)-4-(2-(3-(1-Methylethoxy)-3-oxo-1-propenyl)-phenyl)1,4-dihydro-2,6-dimethyl -3,5-pyridinedicarboxylic acid, diethyl ester m.p. 145°–147° C. (petrol ether) T.l.c. (methylene chloride/Ethyl acetate, 8:2) Rf=0.45
From Intermediate 5 and 1-methylethyl bromide.

5d.
(E)-4-(2-(3-(2-Methylpropyloxy)-3-oxo-1-propenyl)-phenyl)-1,4-dihydro -2,6-dimethyl-3,5pyridinedicarboxylic acid, diethyl ester m.p. 172°–174° C. (petrol ether). T.l.c. (methylene chloride/Ethyl acetate, 8:2) Rf=0.55
From Intermediate 5 and 2-methylpropylbromide.

5e.
(E)-4-(2-(3-Cyclohexyloxy-3-oxo-1-propenyl)-phenyl)1,4-dihydro-2,6-dimethyl-3,5-pyridinedicarboxylic acid diethyl ester m.p. 175°–177° C. (petrol ether) T.l.c. (methylene chloride/Ethyl acetate, 9:1) Rf=0.40
From Intermediate 5 and cyclohexyl bromide.

5f.
(E)-4-(2-(3-Tridecyloxy-3-oxo-1-propenyl)phenyl-1,4dihydro-2,6-dimethyl-3,5-pyridinedicarboxylic acid, diethyl ester m.p.=87°–89° C. T.l.c. (Petrol ether/ethyl acetate, 6:4) Rf.=0.40.
From Intermediate 5 and tridecyl bromide at room temperature

5g.
(E)-4-(2-(3-Cycloheptyloxy-3-oxo-1propenyl)phenyl)-1,4-dihydro-2,6-dimethyl-3,5-pyridinedicarboxylic acid, diethyl ester m.p.=192°–194° C. T.l.c. (methylene chloride/Ethyl acetate, 8:2) Rf.=0.45
From Intermediate 5 and cycloheptyl bromide

5h.
(E)-4-(2-(3-Cyclopentyloxy-3-oxo-1-propenyl)phenyl)-1,4-dihydro-2,6-dimethyl-3,5-pyridinedicarboxylic acid, diethyl ester m.p.=182°–184° c. T.l.c. (Ethyl acetate/cyclohexane, 1:1) Rf.=0.42
from Intermediate 5 and cyclopentyl bromide.

EXAMPLE 6

(E)-4-(2-(3-Octyloxy-3-oxo-1-propenyl)phenyl)-1,4-dihydro-2,6-3,5-pyridinedicarboxylic acid diethyl ester A suspension of the intermediate 5 (0.1 g), octyl methanesulphonate (0.077 g) and potassium carbonate (2 g) in dimethylformamide (5 ml) was stirred at room temperature for 20 hrs. The mixture is poured into water and extracted with ethyl acetate, washed thoroughly with water and dried over Ns₂SO₄. Evaporation of the solvent gave an oil which was triturated with petrol ether and recrystallized from petrol ether to give the title compound as a white solid, (0.04 g). m.p. 110°–112° C. T.l.c. (methylene chloride/Ethyl acetate, 9:1) Rf=0.5

EXAMPLE 7

(E)-4-(2-(3-(1,1-Dimethylethoxy)-3-oxo-1propenyl)-phenyl)-1,4-dihydro-2,6-dimethyl-3,5-pyridinedicarboxylic acid, diethyl ester A suspension of the intermediate 5 (0.2 g) and potassium carbonate (0.07 g) in N,N-dimethylformamide (5 ml) was treated with tert-butyl bromide (0.14 g) and stirred t room temperature for 20 hrs. The mixture was poured into water and extracted with ethyl acetate, washed thoroughly with water nd dried over Na₂SO₄. Evaporation of the solvent gave an oil which was crystallized from petrol ether to give the title compound as a white solid (0.005 g) m.p. 173°–175° C.

EXAMPLE 8

(Z)-4-(2-(3-(1,1-Dimethylethoxy)-3-oxo-1-propenyl)-phenyl-1,4-dihydro -2,6-dimethyl-3,5-pyridinedicarboxylic acid, diethyl ester A solution of the compound of Example 1 (1 g) in dichloromethane (250 ml) was deoxygenated with a stream of nitrogen for 3 min., then left standing, under an atmosphere of nitrogen, in daylight for two weeks. The solution was then evaporated and the solid was recrystallized twice from petrol/diethyl ether (9:1). The white solid obtained (0.2 g) was eluted 5 times on a silica gel plate (CH₂Cl₂) to obtain a colourless oil. Crystallization from petrol ether/diethyl ether (9:1) gave the title compound as a white solid (0.05 g) m.p. 143°–145° C. T.l.c. (methylene chloride/Ethyl acetate, 9:1) Rf=0.40

EXAMPLE 9

9a.

(E)-4-(2-(3-(2,6-Dimethyl-4-heptyloxy)-3-oxo-1-propenyl)phenyl -1,4-dihydro-2,6-dimethyl-3,5-pyridine -dicarboxylic acid, diethyl ester A suspension of Intermediate 5 (2 g), 2,6-dimethyl-4-heptylmethanesulphonate (1.6 g) and potassium carbonate (40 g) in dimethylformamide (30 ml) was stirred at 60° C. for 12 hours. The mixture was poured into water and extracted with ethyl acetate, washed thoroughly with water and dried over Na₂SO₄. Evaporation of the solvent gave a crude oil (3 g) which was eluted on a silica gel column (Diethyl ether/petrol ether, 8:2) to yield the title compound (0.66 g) as a white solid. m.p. 49°–52° C. T.l.c. (Petrol ether/Ethyl acetate, 6:4) Rf.=0.45.

Similarly prepared were:

9b.

(E)-4-(2-(3-(2-Methylcyclohexyloxy)-3-oxo-1-propenyl) phenyl)-1,4-dihydro-2,6-dimethyl-3,5-pyridinedicarboxylic acid, diethyl ester m.p. 165°–166° C. T.l.c. (methylene chloride/Ethyl acetate, 8:2) Rf=0.55.

From Intermediate 5 and 2-methylcyclohexylmethanesulphonate.

EXAMPLE 10

(E)-4-(2-(3-(1,1-Dimethylethoxy)-3-oxo-1-propenyl)-phenyl)-1,4-dihydro -2,6-diethyl-3,5-pyridinedicarboxylic acid diethyl ester A solution of Intermediate 1a (3.2 g) in ethanol (25 ml) was cooled to 0° C. and then trifluoroacetic acid (2 ml) added, followed by a solution of ethyl-3-aminocrotonate (10 g) in ethanol (25 ml). The mixture was stirred at 0° C. for 1 hr, then poured into water and neutralized with 10% sodium bicarbonate and extracted with ethyl acetate. The organic layer was washed with 10% hydrochloric acid then with water and dried over Na₂SO₄. Evaporation of the solvent gave an oil which was eluted on a silica gel column (gradient Ether/petrol, 3:7–7:3) to give the title compound (2 g) as a pale yellow solid. m.p.=154°–155° C. T.l.c. (Petrol ether/ethyl acetate, 1:1) Rf=0.65

EXAMPLE 11

(E)-4-(2-(3-(1,1-Dimethylethoxy)-3-oxo-1-propenyl)-phenyl)-1,4-dihydro -2,6-dimethyl-3,5-pyridinedicarboxylic acid, diethyl ester (a) A mixture of the intermediate 7 (171.5 g), tertiary butylacrylate (67.0 g), tributylamine (97.6 g), palladium acetate (0.94 g) and triphenylphosphine (4.4 g) in dimethylformamide (200 ml) was heated at 110° for 24 hours under nitrogen. The mixture was then cooled, the catalyst removed by filtration and the organic solvent was evaporated to dryness. The residue was dissolved in acetone (700 ml) and the resulting solution was added dropwise to a 0.5% solution of hydrochloric acid (8000 ml) under vigorous stirring. The solid was collected by filtration, washed with water and petroleum ether and dried in vacuo at 60° to give a yellow solid. The solid was recrystallised twice from ethyl acetate (500 ml) to give the title compound (100 g) m.p. 174°–175°. T.l.c. (dichloromethane/ethyl acetate, 8:2) Rf=0.48. (b) In a similar manner the intermediate 8 (91 g) and tertiary butylacrylate (33 g) gave the title compound (46 g).

EXAMPLE 12

(E)-4-(2-(3-(1,1-Dimethylethoxy)-3-oxo-1-propenyl)-phenyl)-1,4-dihydro-2,6-dimethyl-3,5-pyridinedicarboxylic acid diethyl ester A solution of ethyl 3-aminocrotonate (19.5 g) in absolute ethanol (75 ml) was added to a mixture of (E)tert-butyl-2-formyl-cinnamate (11.6 g) and trifluoroacetic acid (11.4 g) in absolute ethanol (90 ml) at −10° to 020 C. The mixture was aged for 1.5 h within this temperature range and then 8% aqueous sodium bicarbonate (150 ml) was added. The product was extracted with tert-butyl methyl ether (3×150 ml), the combined extracts washed with water (2×150 ml) and dried (MgSO₄). Filtration followed by evaporation of solvent gave an oil which was triturated with petroleum ether (50 ml) then filtered to give a granular solid. Crystallisation from ethyl acetate (30 ml) to give the title compound (8.5 g). M.p. 174°–175°.

EXAMPLE 13

(E)-4-(2-(3-(1,1-dimethylethoxy)-3-oxo-propenyl)phenyl)-1,4-dihydro-2,6-dimethyl-3,5-pyridinedicarboxylic acid, methyl ethyl ester Ethyl 3-aminocrotonate (1.3 g) and the intermediate 9 (2.9 g) in ethanol (20 ml) were heated under reflux for 13 hr. The solvent was evaporated and the residual oil was purified by column chromatography (gradient petrol/Ethyl acetate, 7:3-1:1) to give the title compound 0.42 g) as a white solid, m.p.=165°-167° C.

EXAMPLE 14

Pharmaceutical compositions (a) TABLETS

| (I) | mq/tablet |
|---|---|
| Active ingredient | 1 |
| Polyvinylpyrrolidone (PVP) | 20 |
| Lactose B.P. | 127 |
| Magnesium stearate B.P. | 2 |
| Compression weight | 150 |

The drug is granulated by a solution of PVP in ethanol, blended with the excipients and compressed using punches to suit.

| (II) | mg/tablet |
|---|---|
| Active ingredient | 1 |
| Microcrystalline cellulose BPC | 40 |
| Lactose B.P. | 100 |
| Sodium carboxymethylcellulose | 8 |
| Magnesium stearate B.P. | 1 |
| Compression weight | 150 |

The drug is sieved through a suitable sieve, blended with the excipients and compressed using punches to suit.

Tables of other strengths may be prepared by altering the compression weight and using punches to suit. The tablets may be film coated with suitable film forming materials, e.g. methyl cellulose, ethyl cellulose or hydroxypropylmethyl cellulose, using standard techniques. Alternatively the tablets may be sugar coated.

(b) SOFT GELATIN CAPSULES

|  | mg/capsule |
|---|---|
| Active ingredient | 1 |
| Polyethylene glycol (PEG) 400 | 199 |
| Fill weight | 200 |

The drug is dissolved in PEG 400 with stirring and the mix is filled into soft gelatin capsules using a suitable filling machine. Other doses may be prepared by altering the fill weight and if necessary changing the capsule size to accommodate the change in fill weight.

In the above pharmaceutical examples the active ingredient refers to one or more compounds of the general formulae I but is preferably 4-(2-(3-(1,1-dimethylethoxy)-3-oxo-1-propenyl)phenyl)-1,4-dihydro-2,6-dimethyl-3,5-pyridine dicarboxylic acid diethyl ester, and more especially the E isomer thereof.

What we claim is:

1. A composition for treating hypertension, comprising an effective amount of at least one compound of the formula:

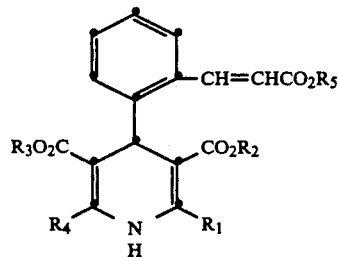

wherein,
$R_1$ and $R_4$ independently represent a $C_{1-4}$ alkyl group;
$R_2$ and $R_3$ independently represent a $C_{1-6}$ straight or branched alkyl chain which may be interrupted by an oxygen atom;
$R_5$ represents a straight or branched chain $C_{1-13}$ alkyl group or a $C_{5-8}$ cycloalkyl group which cycloalkyl group may be substituted by a $C_{1-13}$ alkyl group, and a physiologically acceptable carrier.

2. A composition as claimed in claim 1 in a form suitable for oral, sub lingual, transdermal, parenteral or rectal administration.

3. A composition as claimed in claim 2 in the form of a tablet or capsule for oral administration.

4. A composition as claimed in claim 3 wherein the amount of the oral administration is between about 0.01 to about 50 mg per day.

5. A composition as claimed in claim 3 wherein the amount of the oral administration is between about 0.1 to about 20 mg per day.

6. A composition as claimed in claim 2 for parenteral administration in the form of a bolus injection or continuous infusion.

7. A composition as claimed in claim 6 wherein the amount of the parenteral administration is between 0.005 to about 1 mg per day.

8. A composition as claimed in claim 6 wherein the amount of the parenteral administration is between 0.01 to about 0.5 mg per day.

9. A composition as claimed in claim 2 for transdermal administration in the form of ointments or creams.

10. A composition as claimed in claim 2 for rectal administration in the form of suppositories or retention enemas.

11. A composition as claimed in claim 1 wherein the amount of the compound is between about 0.005 to about 50 mg.

12. A pharmaceutical composition comprising an effective amount of 4-(2-(3-(1,1-dimethylethoxy)-3-oxo-1-propenyl)phenyl) -1,4-dihydro-2-6-dimethyl-3,5-pyridinedicarboxylic acid diethyl ester and a physiologically acceptable carrier.

13. A composition as claimed in claim 12 in a form suitable for oral, sub-lingual, transdermal, parenteral or rectal administration.

14. A composition as claimed in claim 13 for oral administration in the form of a tablet or capsule.

15. A pharmaceutical composition of claim 12, for treating cardiovascular disorders resulting from transmembranal calcium ion flux.

16. A pharmaceutical composition of claim 12, for treating hypertension.

17. A composition as claimed in claim 14 wherein the amount of the oral administration is between about 0.01 to about 50 mg per day.

18. A composition as claimed in claim 14 wherein the amount of the oral administration is between about 0.1 to about 20 mg per day.

19. A composition as claimed in claim 13 for parenteral administration in the form of a bolus injection or continuous infusion.

20. A composition as claimed in claim 19 wherein the amount of the parenteral administration is between 0.005 to about 1 mg per day.

21. A composition as claimed in claim 19 wherein the amount of the parenteral administration is between 0.01 to about 0.5 mg per day.

22. A composition as claimed in claim 13 for transdermal administration in the form of ointments or creams.

23. A composition as claimed in claim 13 for rectal administration in the form of suppositories or retention enemas.

24. A composition as claimed in claim 13 wherein the amount of compound is between about 0.005 to about 50 mg.

25. A method of treating cardiovascular disorders arising from transmembranal calcium ion influx comprising administering to a patient in need of such treatment, an effective amount of the composition of claim 12.

26. A method of treating hypertension comprising administering to a patient in need of such treatment, an effective amount of the composition of claim 1.

27. A method for treating hypertension comprising administering to a patient in need of such treatment, an effective amount of the composition of claim 12.

* * * * *